United States Patent
Dorin et al.

(10) Patent No.: US 11,567,072 B2
(45) Date of Patent: Jan. 31, 2023

(54) LIGAND BOUND MBP MEMBRANES, USES AND METHOD OF MANUFACTURING

(71) Applicant: TeraPore Technologies, Inc., South San Francisco, CA (US)

(72) Inventors: Rachel M. Dorin, San Francisco, CA (US); Spencer Robbins, San Francisco, CA (US); Mark Hurwitz, San Francisco, CA (US)

(73) Assignee: TeraPore Technologies, Inc., South San Francisco, CA (US)

( * ) Notice: Subject to any disclaimer, the term of this patent is extended or adjusted under 35 U.S.C. 154(b) by 0 days.

(21) Appl. No.: 16/487,708

(22) PCT Filed: Feb. 22, 2018

(86) PCT No.: PCT/US2018/019173
§ 371 (c)(1),
(2) Date: Aug. 21, 2019

(87) PCT Pub. No.: WO2018/156731
PCT Pub. Date: Aug. 30, 2018

(65) Prior Publication Data
US 2020/0232978 A1    Jul. 23, 2020

Related U.S. Application Data

(60) Provisional application No. 62/462,161, filed on Feb. 22, 2017.

(51) Int. Cl.
*G01N 33/544* (2006.01)
*B01D 15/38* (2006.01)
(Continued)

(52) U.S. Cl.
CPC ....... *G01N 33/544* (2013.01); *B01D 15/3809* (2013.01); *B01D 67/0093* (2013.01); *B01D 69/02* (2013.01); *B01D 71/80* (2013.01); *B01J 20/265* (2013.01); *B01J 20/28033* (2013.01); *B01J 20/28083* (2013.01);
(Continued)

(58) Field of Classification Search
None
See application file for complete search history.

(56) References Cited

U.S. PATENT DOCUMENTS 3,673,272 A    6/1972    Dean
4,014,798 A    3/1977    Rembaum
(Continued)

FOREIGN PATENT DOCUMENTS

CA    2886437 A1    5/2014
CA    3022510 A1    11/2017
(Continued)

OTHER PUBLICATIONS

P. Jain et al., "Protein Purification with Polymeric Affinity Membranes Containing Functionalized Poly(acid) Brushes." Biomacromolecules, vol. 11 No. 4, pp. 1019-1026, Apr. 12, 2010.
(Continued)

*Primary Examiner* — Clare M Perrin
(74) *Attorney, Agent, or Firm* — Innovators Legal

(57) ABSTRACT

Compositions and methods are described for self-assembled polymer materials having at least one of macro, meso, or micro pores.

17 Claims, 3 Drawing Sheets

(51) Int. Cl.

| | | |
|---|---|---|
| *B01D 67/00* | (2006.01) | |
| *B01D 69/02* | (2006.01) | |
| *B01D 71/80* | (2006.01) | |
| *B01J 20/26* | (2006.01) | |
| *B01J 20/28* | (2006.01) | |
| *B01J 20/32* | (2006.01) | |
| *C07H 1/06* | (2006.01) | |
| *C07H 21/00* | (2006.01) | |
| *C07K 1/22* | (2006.01) | |
| *G01N 33/68* | (2006.01) | |
| *G01N 33/543* | (2006.01) | |

(52) U.S. Cl.
CPC ... *B01J 20/28085* (2013.01); *B01J 20/28092* (2013.01); *B01J 20/321* (2013.01); *B01J 20/3219* (2013.01); *B01J 20/3244* (2013.01); *C07H 1/06* (2013.01); *C07H 21/00* (2013.01); *C07K 1/22* (2013.01); *G01N 33/6803* (2013.01); *B01D 2323/36* (2013.01); *B01D 2325/022* (2013.01); *G01N 33/54353* (2013.01)

(56) References Cited

U.S. PATENT DOCUMENTS

| | | |
|---|---|---|
| 4,399,035 A | 8/1983 | Nohmi et al. |
| 4,666,991 A | 5/1987 | Matsui et al. |
| 4,720,343 A | 1/1988 | Walch et al. |
| 4,880,441 A | 11/1989 | Kesting et al. |
| 5,114,585 A | 5/1992 | Kraus et al. |
| 5,130,024 A | 7/1992 | Fujimoto et al. |
| 5,158,721 A | 10/1992 | Allegrezza et al. |
| 5,647,989 A | 7/1997 | Hayashi et al. |
| 5,700,902 A | 12/1997 | Hancock et al. |
| 5,700,903 A | 12/1997 | Hancock et al. |
| 5,792,227 A | 8/1998 | Kahlbaugh et al. |
| 5,805,425 A | 9/1998 | Peterson |
| 5,907,017 A | 5/1999 | Ober et al. |
| 5,928,792 A | 7/1999 | Moya |
| 6,033,370 A | 3/2000 | Reinbold et al. |
| 6,241,886 B1 | 6/2001 | Kitagawa et al. |
| 6,354,443 B1 | 3/2002 | Moya |
| 6,379,796 B1 | 4/2002 | Uenishi et al. |
| 6,503,958 B2 | 1/2003 | Hughes et al. |
| 6,565,782 B1 | 5/2003 | Wang et al. |
| 6,592,764 B1 | 7/2003 | Stucky et al. |
| 6,592,991 B1 | 7/2003 | Wiesner et al. |
| 6,663,584 B2 | 12/2003 | Griesbach, III et al. |
| 7,056,455 B2 | 6/2006 | Matyjaszewski et al. |
| 7,438,193 B2 | 10/2008 | Yang et al. |
| 7,927,810 B2 | 4/2011 | Togawa et al. |
| 8,025,960 B2 | 9/2011 | Dubrow et al. |
| 8,147,685 B2 | 4/2012 | Pritchard |
| 8,206,601 B2 | 6/2012 | Bosworth et al. |
| 8,294,139 B2 | 10/2012 | Marsh et al. |
| 8,939,294 B2 | 1/2015 | Moore et al. |
| 9,162,189 B1 | 10/2015 | Aamer et al. |
| 9,169,361 B1 | 10/2015 | Aamer |
| 9,193,835 B1 | 11/2015 | Aamer |
| 9,441,078 B2 | 9/2016 | Aamer |
| 9,469,733 B2 | 10/2016 | Aamer et al. |
| 9,527,041 B2 | 12/2016 | Wiesner et al. |
| 10,711,111 B2 | 7/2020 | Wiesner et al. |
| 10,912,868 B2 | 2/2021 | Ushiro et al. |
| 2003/0073158 A1 | 4/2003 | Ma |
| 2003/0171560 A1 | 9/2003 | Peters |
| 2003/0226818 A1 | 12/2003 | Dunbar et al. |
| 2004/0065607 A1 | 4/2004 | Wang et al. |
| 2004/0122388 A1 | 6/2004 | McCormack et al. |
| 2004/0126778 A1 | 7/2004 | Lemmens et al. |
| 2004/0129678 A1 | 7/2004 | Crowley et al. |
| 2004/0138323 A1 | 7/2004 | Stenzel-Rosebaum et al. |
| 2004/0242822 A1 | 12/2004 | Gawrisch et al. |
| 2006/0014902 A1 | 1/2006 | Mays et al. |
| 2006/0085062 A1 | 4/2006 | Lee et al. |
| 2006/0094598 A1 | 5/2006 | Simon |
| 2006/0151374 A1 | 7/2006 | Wu et al. |
| 2006/0283092 A1 | 12/2006 | Chinone |
| 2007/0029256 A1 | 2/2007 | Nakano et al. |
| 2007/0265174 A1 | 11/2007 | Schlenoff |
| 2007/0287241 A1 | 12/2007 | Takahashi et al. |
| 2008/0097271 A1 | 4/2008 | Lo et al. |
| 2008/0193818 A1 | 8/2008 | Mays |
| 2008/0261255 A1 | 10/2008 | Tolosa et al. |
| 2009/0173694 A1 | 7/2009 | Peinemann et al. |
| 2009/0181315 A1 | 7/2009 | Spatz et al. |
| 2009/0208726 A1 | 8/2009 | Yang et al. |
| 2009/0209726 A1 | 8/2009 | Matsumoto et al. |
| 2009/0239381 A1 | 9/2009 | Nishimi et al. |
| 2010/0051546 A1 | 3/2010 | Vuong et al. |
| 2010/0108599 A1 | 5/2010 | Vizvardi et al. |
| 2010/0167271 A1 | 7/2010 | Ryan |
| 2010/0181288 A1 | 7/2010 | Tang et al. |
| 2010/0219383 A1 | 9/2010 | Eklund |
| 2010/0224555 A1 | 9/2010 | Hoek et al. |
| 2011/0130478 A1 | 6/2011 | Warren et al. |
| 2011/0240550 A1 | 10/2011 | Moore et al. |
| 2011/0275077 A1 | 11/2011 | James et al. |
| 2012/0048799 A1 | 3/2012 | Na et al. |
| 2012/0318741 A1 | 12/2012 | Peinemann et al. |
| 2013/0053748 A1 | 2/2013 | Cotton |
| 2013/0112613 A1 | 5/2013 | Kang et al. |
| 2013/0129972 A1 | 5/2013 | Xu |
| 2013/0193075 A1 | 8/2013 | Liang et al. |
| 2013/0344375 A1 | 12/2013 | Brant et al. |
| 2014/0005364 A1 | 1/2014 | Gottschall et al. |
| 2014/0217012 A1 | 8/2014 | Wiesner et al. |
| 2014/0363572 A1 | 12/2014 | Moll et al. |
| 2014/0371698 A1 | 12/2014 | Chang et al. |
| 2015/0151256 A1 | 6/2015 | Abetz et al. |
| 2015/0343395 A1 | 12/2015 | Aamer et al. |
| 2015/0343398 A1 | 12/2015 | Aamer et al. |
| 2016/0023171 A1* | 1/2016 | Phillip ............... C08J 9/00 210/650 |
| 2016/0229969 A1 | 8/2016 | Wiesner et al. |
| 2016/0288062 A1 | 10/2016 | Ait-Haddou et al. |
| 2016/0319158 A1 | 11/2016 | Fleury et al. |
| 2016/0375409 A1 | 12/2016 | Stasiak et al. |
| 2017/0022337 A1 | 1/2017 | Wiesner et al. |
| 2017/0105877 A1 | 4/2017 | Buteux et al. |
| 2017/0327649 A1 | 11/2017 | Wiesner et al. |
| 2018/0043314 A1 | 2/2018 | Onyemauwa et al. |
| 2018/0043656 A1 | 2/2018 | Song et al. |
| 2019/0233307 A1 | 8/2019 | Fujimura et al. |
| 2020/0238227 A1 | 7/2020 | Dorin et al. |
| 2020/0339770 A1 | 10/2020 | Wiesner et al. |
| 2021/0040281 A1 | 2/2021 | Dorin et al. |

FOREIGN PATENT DOCUMENTS

| | | |
|---|---|---|
| CN | 201211329 Y | 3/2009 |
| CN | 101460203 A | 6/2009 |
| CN | 101516481 A | 8/2009 |
| CN | 101969902 A | 2/2011 |
| CN | 102224163 A | 10/2011 |
| CN | 102892486 A | 1/2013 |
| CN | 103797053 A | 5/2014 |
| CN | 104159657 A | 11/2014 |
| CN | 104768506 A | 7/2015 |
| CN | 105273211 A | 1/2016 |
| CN | 105536580 A | 5/2016 |
| CN | 106344539 A | 1/2017 |
| DE | 102012207338 A1 | 11/2013 |
| DE | 102014213027 A1 | 1/2016 |
| EP | 2160946 A1 | 3/2010 |
| EP | 2703016 A1 | 3/2014 |
| EP | 2705077 A2 | 3/2014 |
| EP | 2977101 A1 | 1/2016 |
| EP | 3056260 A1 | 8/2016 |
| EP | 3284529 A1 | 2/2018 |
| EP | 3541500 A1 | 9/2019 |
| EP | 3544720 A1 | 10/2019 |

(56) References Cited

FOREIGN PATENT DOCUMENTS

| | | |
|---|---|---|
| EP | 3658262 A1 | 6/2020 |
| FR | 3037071 A1 | 12/2016 |
| JP | 54-145766 A | 11/1979 |
| JP | 04-022428 A | 1/1992 |
| JP | 09-048861 A | 2/1997 |
| JP | 2002-537422 A | 11/2002 |
| JP | 2005-500132 A | 1/2005 |
| JP | 2006-175207 A | 7/2006 |
| JP | 2011-117956 A | 6/2011 |
| JP | 2011-131208 A | 7/2011 |
| JP | 2011-189229 A | 9/2011 |
| JP | 2012-246162 A | 12/2012 |
| JP | 2015-083299 A | 4/2015 |
| JP | 2015-167914 A | 9/2015 |
| JP | 2016-514049 A | 5/2016 |
| JP | 2016-526089 A | 9/2016 |
| JP | 2017-153616 A | 9/2017 |
| JP | 2018-500401 A | 1/2018 |
| JP | 2019-514687 A | 6/2019 |
| KR | 10-2009-0088124 A | 8/2009 |
| KR | 10-2012-0047269 A | 5/2012 |
| KR | 10-2012-0124412 A | 11/2012 |
| KR | 2012-0124412 A | 11/2012 |
| KR | 10-2016-0020404 A | 2/2016 |
| KR | 10-2018-0019059 A | 2/2018 |
| SG | 10201706492 A | 3/2018 |
| SG | 11201904425 Y | 6/2019 |
| SG | 11202000664 Y | 2/2020 |
| WO | 2005/082501 A1 | 9/2005 |
| WO | 2005/091755 A2 | 10/2005 |
| WO | 2008/034487 A1 | 3/2008 |
| WO | 2010/051150 A1 | 5/2010 |
| WO | 2011/098851 A1 | 8/2011 |
| WO | 2011/111679 A1 | 9/2011 |
| WO | 2011/123033 A1 | 10/2011 |
| WO | 2012/151482 A2 | 11/2012 |
| WO | 2014/164793 A2 | 10/2014 |
| WO | 2015/048244 A1 | 4/2015 |
| WO | 2015/168409 A1 | 11/2015 |
| WO | 2015/188225 A1 | 12/2015 |
| WO | 2016/023765 A1 | 2/2016 |
| WO | 2016/031834 A1 | 3/2016 |
| WO | 2016/066661 A1 | 5/2016 |
| WO | 2017/189697 A1 | 11/2017 |
| WO | 2018/043209 A1 | 3/2018 |
| WO | 2018/055801 A1 | 3/2018 |
| WO | 2018/093714 A1 | 5/2018 |
| WO | 2018/097988 A1 | 5/2018 |
| WO | 2019/023135 A1 | 1/2019 |
| WO | 2019/178045 A1 | 9/2019 |
| WO | 2019/178077 A1 | 9/2019 |
| WO | 2019/195396 A1 | 10/2019 |

OTHER PUBLICATIONS

D. Keskin, et al., "Postmodification of PS-b-P4VP Diblock Copolymer Membranes by Arget ATRP." Langmuir, vol. 30, pp. 8907-8914, Jun. 19, 2014.
E. Gifford et al., "Sensitivity Control of Optical Fiber Biosensors Utilizing Turnaround Point Long Period Gratings with Self-Assembled Polymer Coatings." Proceedings of the SPIE, vol. 6659, pp. 66590D-1-66590D-9, Sep. 30, 2007.
A Bruil et al., "The Mechanisms of Leukocyte Removal by Filtration." Transfusion Medicine Reviews vol. IX No. 2, pp. 145-166, Apr. 1995.
A. A. Shukla et al., "Recent Advances in Large-Scale Production of Monoclonal Antibodies and Related Proteins." Trends in Biotechnology, vol. 28, No. 5, pp. 253-261, 2010.
A.S. Devonshire et al., "Towards Standardisation of Cell-Free DNA Measurement in Plasma: Controls for Extraction Efficiency, Fragment Size Bias and Quantification." Anal. Bioanal. Chem., vol. 406, pp. 6499-6512, 2014.

Behler, Ansgar (Edited by), "Poren," Rompp Verlag, Rompp online 4.0, Aug. 2005, retrieved from Internet: URL: https://roempp.thieme.de/roempp4.0/do/data/RD-16-03734.
Breiner et al, "Structural Characterization of the "Knitting Pattern" in Polystyrene-block-poly(ethylene-co-butylene)-block-poly(methyl methacrylate) Triblock Copolymers", Macromolecules 1998, 31, 135-141.
Clodt et al., "Performance study of isoporous membranes with tailored pore sizes", Journal of Membrane Science, vol. 495, Jul. 29, 2015, pp. 334-340.
Dai et al., "Fabrication of 2D ordered structure of self-assembled block copolymers containing gold nanoparticles," Journal of Crystal Growth, vol. 288, No. 1, pp. 128-136, Feb. 2, 2006.
Doan Minh Y Nhi, "Investigation of the Effects of UV-Crosslinking on Isoporous Membrane Stability." KTH Chemical Science and Engineering, pp. 1-46, 2011.
F. A. Carey, Ornanic Chemistry, Fifth Edition, pp. 859-860, 2003.
Fink, Johannes Karl. Handbook of Engineering and Specialty Thermoplastics. 2011. vol. 2, Water Soluble Polymers. Chapter 7. p. 189-192. (Year: 2011).
H. Ahlbrecht et al., "Stereoselective synthesis." Methods of Organic Chemistry. Houben-Weyl, vol. E 21 a, 4th Edition Supplement, 1995.
H. Sai et al., "Hierarchical Porous Polymer Scaffolds from Block Copolymers." Science, vol. 341, pp. 530-533, Aug. 2, 2013.
Hanselmann, Blockcopolymere, ROMPP Online, Version 3.37, Dokumentkennung RD-02-02007. Jul. 1, 2009.
Hilke et al., "Block copolymer/homopolymer dual-layer hollow fiber membranes", Journal of Membrane Science, vol. 472, Aug. 23, 2014, pp. 39-44.
Hoek et al., Physical-chemical properties, separation performance, and fouling resistance of mixed-matrix ultrafiltration member, Desalination, Elsevier, vol. 283, pp. 89-99. May 4, 2011.
Huang Yan et al: "Highly Ordered Mesoporous Carbonaceous Frameworks from a Template of a Mixed Amphiphilic Triblock-Copolymer System of PEO-PPO-PEO and Reverse PPO-PEO-PPO", Chemistry—An Asian Journal, vol. 2, No. 10, Oct. 1, 2007 (Oct. 1, 2007), pp. 1282-1289.
J. I. Clodt et al., "Carbohydrates as Additives for the Formation of Isoporous PS-b-P4VP Diblock Copolymer Membranes." Macromolecular Rapid Communications, vol. 34, 190-194, 2013.
J. Suzuki et al., "Morphology of ABC Triblock Copolymer/Homopolymer Blend Systems." Journal of Polymer Science Part B: Polymer Physics vol. 40 pp. 1135-1141 Apr. 22, 2002.
Julie N.L. Albert et al. "Self-assembly of block copolymer thin films", Materialstoday, vol. 13, is. Jun. 6, 2010, pp. 24-33.
Jung et al., Structure Formation of Integral Asymmetric Composite Membranes of Polystyrene-block-Poly(2-vinylpuridine) on a Nonwoven, Macromolecular Materials and Engineering, vol. 297, No. 8, pp. 790-798. Feb. 9, 2012.
Kanegsberg, "Washing, Rinsing, and Drying: Items to Consider for the Optimization of Your Cleaning Process," https://www.materialstoday.com/metal-finishing/features/washing-rinsing-and-drying-items-to-consider-for/, Sep. 1, 2005. p. 2, paragraph 6.
Karunakaran et al. "IsoporousIPS-b-PEO ultrafiltration membranes via self-assembly and water-induced phase separatioln" Journal of Membrane Science, vol. 453 Issue 1 (Nov. 16, 2013): pp. 471-477.
Khademi, M. Application of Tubular Crssflow Microfiltration in Harvesting Microalgae. LSU Master's Theses. 2014, pp. 39-43.
Kharitonov et al., "Surface modification of polymers by direct fluorination: A convenient approach to improve commercial properties of polymeric articles," Pure Appl. Chem., vol. 81, No. 3, pp. 451-471, 2009.
Laboratory-Equipment.com, "Applications for Laboratory Ovens Across the Sciences." https://www.laboratory-equipment.com/blog/all-laboratory-equipment-blogs/applications-for-laboratory-ovens-across-the-sciences/, Oct. 15, 2015, p. 1, section "Standard and Specialized Lab Oven Applications".
Lawrence E. Nielsen, "Cross-Linking-Effect on Physical Properties of Polymers." Journal of Marcomolecular Science Part C, vol. 3(1), pp. 69-103, 2008.
Li Yuk Mun et al: "Asymmetric Membranes from Two Chemically Distinct Triblock Terpolymers Blended during Standard Membrane

(56) References Cited

OTHER PUBLICATIONS

Fabrication", Macromolecular Rapid Communications, vol. 37, No. 20, Oct. 1, 2016 (Oct. 1, 2016), pp. 1689-1693.

Lubomir et al., "Deposition of polymeric perfluored thin films in proton ionic membranes by plasma processes," Applied Surface Science, vol. 254, pp. 173-176, 2007.

Mu X. et al., Nano-porous Nitrocellulose Liquid Bandage Modulates Cell and Cytokine Response and Accelerates Cutaneous Wound Healing in a Mouse Model. Carbohydr Polym., Sep. 25, 2015, vol. 136, pp. 618-629.

N. Lefevre et al., "Self-Assembly in Thin Films of Mixtures of Block Copolymers and Homopolymers Interacting by Hydrogen Bonds." Macromolecules, vol. 43, No. 18, pp. 7734-7743 Aug. 17, 2010.

Peinemann et al, "Asymmetric superstructure formed in a block copolymer via phase separation", Nature Materials, V6, Dec. 2007 (Peinemann NLP).

Phillip, W., et al., Tuning Structure and Properties of Graded Triblock Terpolymer-Based Mesoporous and Hybrid Films, Nano Letters, Jun. 7, 2011, Nov. 11, pp. 2892-2900.

Qiu et al. "Selective Separation of Similarly Sized Proteins with Tunable Nanoporous Block Copolymer Membranes." ACS Nano. vol. 7, No. 1, 2013. p. 768-776 (Year: 2013).

R. van Reis et al., "High Performance Tangential Flow Filtration." Biotechnology and Bioengineering, vol. 56, No. 1, pp. 71-82, Oct. 5, 1997.

Radjabian, Polymer, 55 (2014), 2986-2997 (Year: 2014).

Ren et al, J. Am. Chem. Soc, 1998, 120, 6830-6831 (Year: 1998).

Roland et al., "Supplementary Information Block Copolymer/ Homopolymer Dual-Layer Hollow Fiber Membranes Imaging and Characterization Lab and c Water Desalination", Aug. 23, 2014, pp. 1-3.

S. Breitbach et al., "Direct Quantification of Cell-Free, Circulating DNA from Unpurified Plasma." PLOS One, vol. 9, Issue 3, e87838. pp. 1-11.

S. P. Nunes et al., "From Micelle Supramolecular Assemblies in Selective Solvents to Isoporous Membranes." Langmuir, DOI 10.1021/ la201439P, Jun. 28, 2011.

S. Rangou et al., "Self-Organized Isoporous Membranes with Tailored Pore Sizes." Journal of Membrane Science, vol. 451, pp. 266-275, 2014.

Shahkaramipour et al., "Membranes with Surface-Enhanced Antifouling Properties for Water Purification," Membranes, vol. 7, pp. 13, 2017.

Tiraferri et al., Binding Silver and Silica Nanoparticles to Polymeric Membrane Surfaces for Novel Anti-Biofouling Properties, ACS Division Proceedings, Division of Polymer Chemistry, Meeting 242, Aug. 28-Sep. 1, 2011, Denver, Co, USA. Sep. 1, 2011.

Volker Abetz "Isoporous Block Copolmer membranes", Macromolecular Rapid Communications, vol. 36, No. 1, Nov. 29, 2014 (Nov. 29, 2014), pp. 10-22.

Wang Zhaogen et al: "Isoporous membranes with gradient porosity by selective swelling of UV-crosslinked block copolymers", Journal of Membrane Science, vol. 476, Feb. 1, 2015 (Feb. 1, 2015), pp. 449-456.

Y Nhi et al., "Investigation of the Effect of UV-Crosslin King on Isoporous Membrane Stability", Chemical Science and Engineering, vol. 46, Dec. 12, 2011.

Yizhou Zhang et al: "Nanoporous membranes generated from self-assembled block polymer precursors: Quo Vadis?", Journal of Applied Polymer Science, vol. 132, No. 21, Jun. 5, 2015.

Yizhou Zhang, et al., "Microfiltration and Ultrafiltration Membrane Science and Technology". Journal of Applied Polymer Science, app. 41683, on. Jan. 17, 2015.

Young et al., Robert J., Introduction to Polymers, Third Edition, CRC Press 2011, pp. 6-9 and 456-457.

* cited by examiner

LIGAND BOUND MBP MEMBRANES, USES AND METHOD OF MANUFACTURING

CROSS REFERENCE TO RELATED APPLICATIONS

This application is a national stage of International Patent Application No. PCT/US2018/019173, filed Feb. 22, 2018, which claims the benefit of U.S. Provisional Application No. 62/462,161, filed Feb. 22, 2017, the contents of each of which are incorporated herein by reference in their entirety.

FIELD OF THE INVENTION

The invention relates to ligand-bound, multi-block polymer ("MBP") isoporous materials, their preparation and uses in analytical, detection and separation protocols for the laboratory, scale-up or commercial environment, such as, but not limited to separation techniques necessary for protein purification and production processes, and in-particular, as replacements for column-based affinity separation, as well as sensors for monitoring and detecting analytes of interest.

BACKGROUND OF THE INVENTION

Protein purification is a critical and challenging aspect in the biomolecule separations market, from R&D to large-scale manufacturing. It is widely acknowledged that a key bottleneck for the entire protein purification process involves the numerous separation protocols. One aspect of current protein purification involves affinity separations that use porous membranes, or supported porous materials with interconnected pores of more than one size regime. Often, the porous membranes useful for affinity separations are formed by linking reactive groups (carboxylic acid groups are disclosed among others) to biological active agents, e.g., Protein A amongst others. The membrane is made of polymeric material. Reactive groups can be directly part of the polymer or formed via precursors which form the reactive group by subsequent treatment.

The membranes are also formed by attaching (directly or via a linking moiety) an affinity ligand to a reactive bifunctional monomer and polymerizing the affinity ligand/monomer material alone or in the presence of additional monomers and a "porogen," such as an alcohol. To protect the affinity ligand during the polymerization, it can be protected by a cleavable moiety which, after polymerization, is removed by treatment e.g. with acid.

Affinity separations can include membranes that have a poly (aryl ether ketone), and a "porogen," e.g., a polyimide, that have been casted and then pores are formed in the casting by selectively removing the polyimide by chemical reaction. The resulting porous membrane is then functionalized by reacting the ketone groups in the membrane with an amine bearing an additional attachment group which can be used in further attachment of various species such as proteins.

Porous membranes for affinity separations have also been made from copolymers (including copolymers containing (in general) styrene derivatives and alkyl acrylate derivatives) and attached via an amide linkage to "affinity ligand" materials including proteins. The copolymers are not block copolymers that self-assemble, or functionalized by/with hydroxyl or amino groups by reaction with various "activators," which are then further reacted with affinity ligands (protein A is disclosed).

Other affinity membranes are formed by casting a solution block copolymer (PEO/PPO polyether) and a polysulfone in an organic solvent, followed by a water quenching step. The resulting polymeric membrane has hydroxyl groups on the surface which are then further derivatized to covalent bound biological materials to the membrane. The copolymer is then derivatized prior to casting and the hydroxyl groups freed after membrane formation.

Membranes from microphase separation structures are prepared from self-assembled block polymer derived from styrenes and an alkyl acrylate with a "polar group. Copolymer membranes containing a carboxyl group-bearing monomer unit where one or more of sugars, lipids, proteins, peptides and composites thereof are also known.

Interest in membrane chromatography has gradually increased over the past decade, but widespread commercial adoption of membrane chromatography as a replacement for column chromatography has been hindered by limitations in both the variety of available materials platforms and a lack of significant technical advances in membrane structure and performance. In particular, commercially available membrane chromatography materials have been built on conventional membrane structures, which suffer from broad pore size distributions. This pore size variation causes uneven flow patterns across the membrane, broadening breakthrough curves and diminishing media capacity. In current practice, breakthrough curves are sharpened by stacking layers of membrane together so the average permeability along streamlines is rendered more uniform. Chromatography devices in which a stack of membrane layers replaces the more typical column of packed beads have been proposed (See for example WO2000050888A1) but the depth of the column is severely limited by the pressure required to drive flow through a stack of membranes with submicron pores.

However, despite major progress in understanding protein expression, structure, and function, the purification of proteins from complex mixtures remains a significant challenge for protein developers at all process scales and it requires an array of separation techniques.

DETAILED DESCRIPTION OF THE INVENTION

Figure 1:
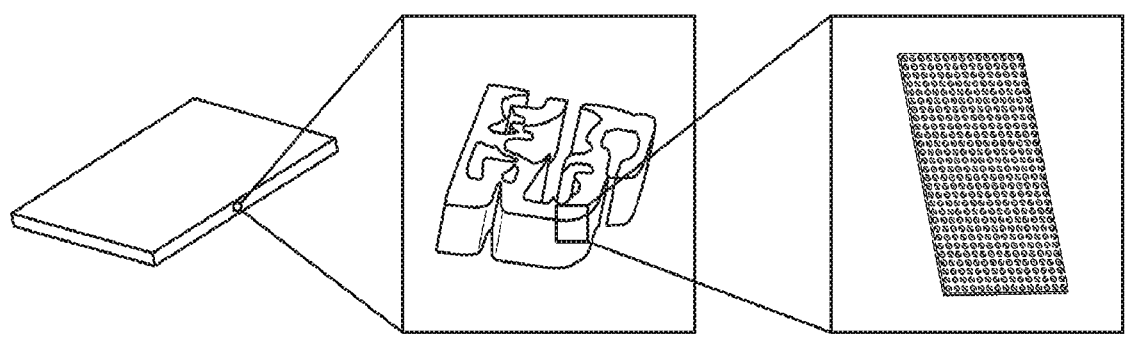
FIG. 1 is an illustration depicting general hierarchical porosity of a MBP material. Multiple length scales of porosity are depicted.
Figure 2:
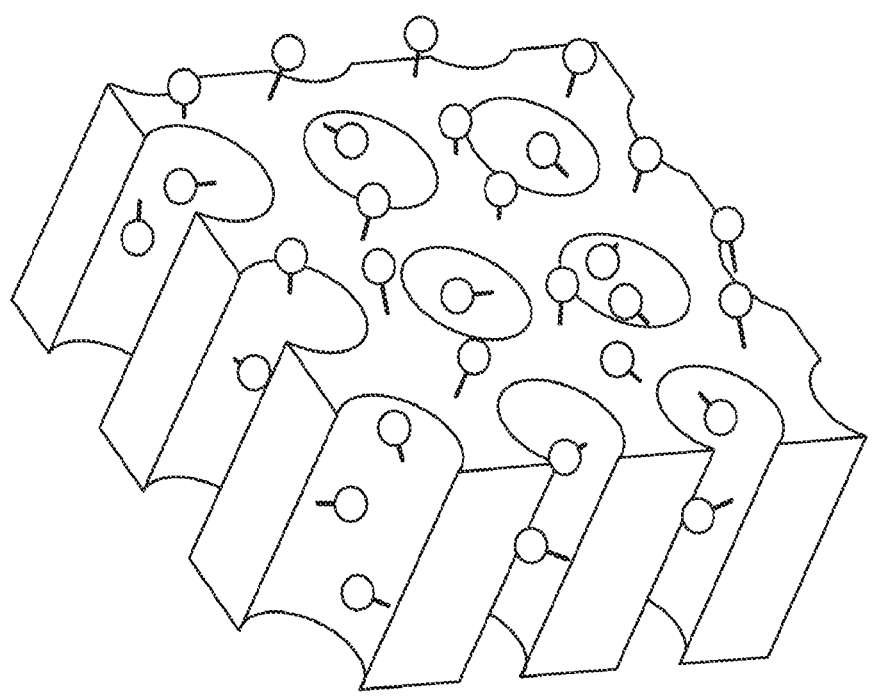
FIG. 2 is an illustration depicting affinity ligands on the surface of a porous block copolymer film.
Figure 3:
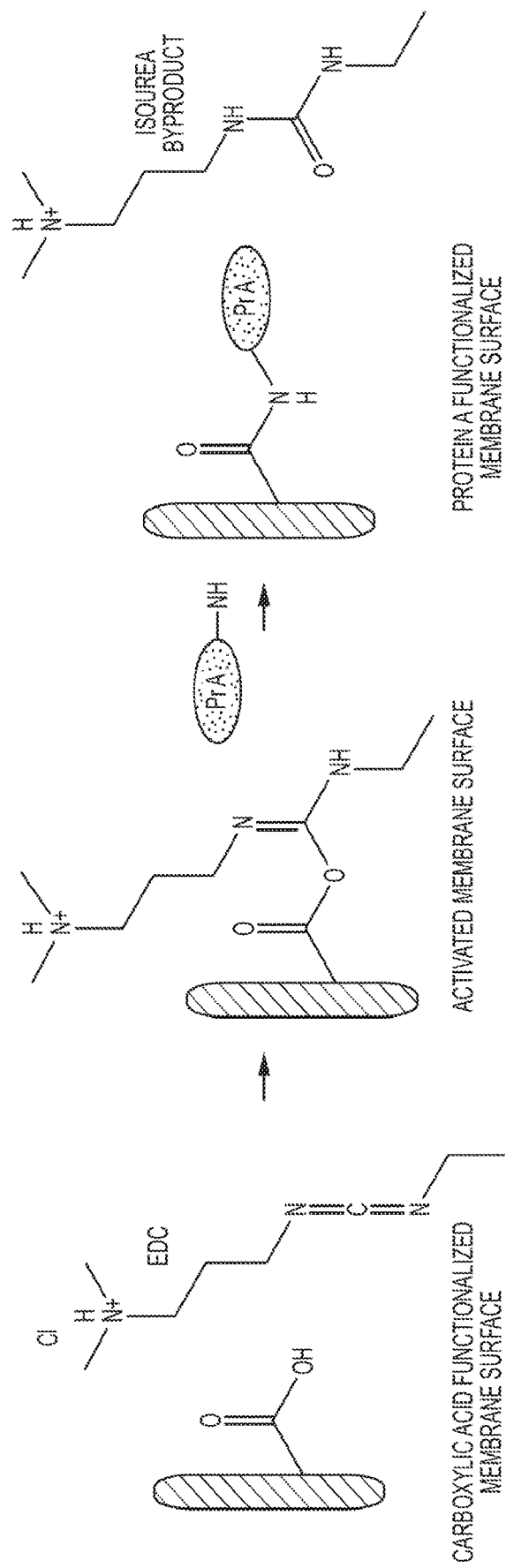
FIG. 3 is an illustration depicting membrane surface modication with Protein A ligand with EDC

Block copolymer, terpolymer, tetrapolymer, collectively multi-block polymer (MBP) materials/structures are disclosed with at least a portion of the material/structure formed through self-assembly such that the material or structure is hierarchically porous (has pores of multiple length scales). The self-assembled polymer materials contain at least one of macro, meso or micro pores, at least some of which are isoporous. Micropores are defined as having a diameter of 0.1 to 1 nm. Mesopores are defined as having a diameter of 1 nm to 200 nm. Macropores are defined as having a diameter of 200 nm to 1000 μm.

In one embodiment the self-assembled polymer materials contain mesopores or micropores that have a narrow pore size distribution, and the MBP material or structure is modified partly or completely with an affinity ligand (or linker which is used to attach an affinity ligand). The polymer materials are formed into films, supported or unsupported, pleated or non-pleated, three-dimensional pleated configurations that are planar, circumferential or spiral in shape, as liners or inserts for various vessels, tubes, or cuvettes. The material can be formed into various shapes, e.g. beads, spheres, or multidimensional solid media.

In some embodiments, the MBPs comprise mesopores. In an embodiment, the mesopores are in the range of about 1 nm to about 200 nm. In an embodiment the mesopores are in the range of about 3 nm to about 200 nm. In an embodiment the mesopores are in the range of about 5 nm to about 200 nm. In an embodiment the mesopores are in the range of about 5 nm to about 100 nm. In an embodiment, the mesopores are in the range of about 5 nm to about 50 nm. In some embodiments, the MBPs comprise micropores. In an embodiment, the micropores are in the range of about 0.1 nm to about 1 nm.

In some embodiments, the MBPs comprise macropores. In an embodiment, the macropores are in the range of about 200 nm to about 1000 μm. In an embodiment, the macropores are in the range of about 200 nm to about 100 μm. In an embodiment, the macropores are in the range of 200 nm to about 10 μm. In an embodiment, the macropores are in the range of 1 μm to about 10 μm. In an embodiment, the macropores are in the range of about 500 nm to about 10 μm.

The MBPs structure/material of the present invention provide a solution to difficulties with existing column affinity chromatography by using the high-capacity MBP membrane structure/films that are modified to partly or completely function as membrane adsorbers with the same or better separation qualities in a fraction of the processing time relative to existing column affinity chromatography media. Current downstream purification processes utilize multiple steps and is performed batch-wise. The first step in the purification line is a column-based affinity separation, which is widely acknowledged as a key bottleneck for the entire process. The affinity column represents nearly 25% of the total process time, leaving downstream equipment idle and resulting in low manufacturing efficiencies. This step also represents the largest labor expenditure in the entire purification line. Furthermore, the high volume of consumables required for column chromatography contributes considerably to the high costs of protein development and manufacturing. The existing bottleneck caused by existing column affinity chromatography is alleviated through dramatic decrease in processing time with corresponding reductions in manufacturing costs, and at the same time increasing production efficiencies when the MBPs structure/material membrane/film adsorbers of the present invention are used.

In addition to debottlenecking existing purification processes, the present invention provides process improvements by making possible highly uniform flow through a single layer of membrane. In configurations where isoporous meso or micro pores form a continuous layer on the downstream surface of the membrane, these pores provide a uniform flow resistance much greater than that provided by the larger heterogeneous pores, although smaller than the resistance to flow that occurs in a paced column of similar pore size. When the membrane is packaged as a filtration device utilizing a small number of membrane layers (preferably no more than three, more preferably one) the resistance of the isoporous layer causes the flow velocity to be uniform everywhere, thus efficiently utilizing all of the binding sites. Further, in such a device, which, for example, can be a cartridge containing a pleated pack, a crossflow cassette or module containing flow channels bounded by flat sheets of membrane, or a spiral would cartridge such as is common in the water filtration industry, particulate or large molecule filtration can be combined in one step with chromatographic separation, thus reducing the total number of unit operations required.

The multi-block polymers of the present invention rely on self-assembly techniques to form the membrane films, such as those disclosed in U.S. Pat. No. 9,527,041, or the hybrid material of International Publication No. WO20 15048244, each of which incorporated by reference in its entirety.

Or, as described in Hierarchically Porous Materials from Block Copolymers, Dorin et al., the entirety of which are incorporated by reference. The membrane films are modified to include bound ligands, and provide high selectivity contemporaneously with high through-put. The process provides the films with a hierarchically porous structure having very high surface areas and combines macroporous continuous domains with mesoporous wall structures in a single, scalable material. The macroporous structural features provide for convective solution flow, offering rapid processing, while the mesoporous walls create high surface areas, offering the unique potential for high density affinity functionalizations. The addition of high-capacity potential through mesoporous matrix structures makes them suitable for industrial application in the biomolecule separations market.

The combination of uniform mesoporosity and macroporosity in the multi-block polymers of the present invention provide membrane of high flux and high surface area. The macroporous regions allow high flux while the uniform mesopores provide high surface areas and uniform flow distribution. The affinity ligand on the membrane surface provides a platform for affinity-based interactions of species/analytes of interest with the membrane.

The MBP material of the present invention, whether in film or three-dimensional configuration, are formed from one of purely organic templates, hybrid materials, combinations thereof, alone, or combined with surface located or embedded nanoparticles, and optionally functionalized.

The present invention utilizes the self-assembly technique for preparing the multi-block polymers of the present invention with at least one block containing functional groups to form hierarchically porous membranes with very high surface areas. At least one block in the MBP of the membrane is modified with covalent or noncovalent links with an affinity ligand. Such structures do not require a substrate for formation and combine macroporous continuous domains with mesoporous wall structures in a single, scalable structure. The macroporous structural features provide for improved convective solution flow, offering rapid processing, while the mesoporous walls create high surface areas, offering the potential for high density surface functionalizations. The addition of high-capacity potential through mesoporous matrix structures has highly promising implications for industrial application in the protein separations market compared to known membranes.

In some applications the isoporous layer occupies the entirety of the downstream surface of the membrane, especially in embodiments where the material is a membrane that is pleated.

The inventive hierarchically porous multi-block polymer ("MBP") material/structure is functionalized with an affinity ligand. The MBP contains two or more chemically distinct blocks (A-B), also A-B-C or B-A-C terpolymers, or are higher order multi-block copolymer systems of the form A-B-C-B, or A-B-C-D, or A-B-C-B-A, or A-B-C-D-E, or other variable arrangements of these higher order systems. The multiblock copolymers can be synthesized by methods known in the art. Some examples of synthetic methods for the multiblock copolymers include: anionic polymerization, cationic polymerization, reversible addition-fragmentation chain-transfer polymerization, atom-transfer radical polymerization, and any combinations of the listed synthetic methods. Each block can, but does not necessarily contain a mixture of chemistries, provided adjacent blocks are sufficiently chemically distinct, thus enabling self-assembly. In an embodiment, at least one block of at least one block copolymer comprising the MBP comprises a hydrophilic or hydrogen-bonding block chemistry. For example, suitable hydrophilic or hydrogen bonding block chemistries include: poly((4-vinyl)pyridine), poly((2-vinyl) pyridine), poly(ethylene oxide), poly(methacrylate), poly(methyl methacrylate), poly(dimethylethyl amino ethyl methacrylate), poly (acrylic acid), poly(dimethyl acrylamide), poly(styrene sulfonate), poly(2-hydroxyethyl methacrylate), poly(acrylamide) and poly(hydroxystyrene)). In some embodiments, at least one block copolymer comprising the MBP further comprises at least one hydrophobic block chemistry. Examples of suitable hydrophobic block chemistries include: poly(styrene), poly(isoprene), poly(butadiene), poly(ethylene), poly(propylene). Examples of suitable block copolymers include for example, poly(isoprene-b-styrene-b-4-vinyl-pyridine), poly(isoprene-b-styrene-b-2-vinyl-pyridine), poly(isoprene-b-styrene-b-ethylene oxide), poly(isoprene-b-styrene-b-methacrylate), poly(isoprene-b-styrene-b-methyl methacrylate), poly(isoprene-b-styrene-b-dimethylethyl amino ethyl methacrylate), poly(isoprene-b-styrene-b-acrylic acid), poly(isoprene-b-styrene-b-dimethylethyl amino ethyl methacrylate), poly(isoprene-b-styrene-b-dimethyl acrylamide), poly(isoprene-b-styrene-b-styrene sulfonate), poly(isoprene-b-styrene-b-2-hydroxyethyl methacrylate), poly(isoprene-b-styrene-b-acrylamide), poly(isoprene-b-styrene-b-hydroxystyrene), poly(styrene-b-4-vinylpyridine), poly(styrene-b-2-vinylpyridine), poly(styrene-b-ethylene oxide), poly(styrene-b-methacrylate), polystyrene-b-methyl methacrylate), poly(styrene-b-dimethylethyl amino ethyl methacrylate), poly(styrene-b-acrylic acid), poly(styrene-b-dimethyl acrylamide), poly(styrene-b-styrene sulfonate), poly(styrene-b-2-hydroxyethyl methacrylate), poly(styrene-b-acrylamide), poly(styrene-b-hydroxystyrene), poly(propylene-b-4-vinylpyridine), poly(styrene-b-2-vinylpyridine-b-isoprene-hydroxystyrene), poly(styrene-b-butadiene-b-dimethyl acrylamide-b-isoprene-styrene-4-vinylpyridine). The above polymers are listed as illustrative examples and other chemistries, combinations and block numbers and orientations are possible as long as the materials meet the structural characteristics of the invention.

The blocks are not necessarily separated by a single unit or several units of a differing chemistry which might not be considered a distinct "block." Blocks can but are not necessarily linked with a gradient of chemistries between blocks (i.e. there is no sharp transition in chemistry at a single unit in the copolymer). Hierarchically porous materials generally have interconnected pores of more than one size regime. The films contain mesopores, as well as macropores. The mesopores exhibit a narrow pore size distribution due to the self-assembly of the block copolymers during material or structure formation, such as a film. The materials have an overall isotropic or asymmetric structure. The membrane surface is partially or completely surface modified with an affinity ligand, shown below.

Affinity ligands are molecules that are capable of binding with very high affinity to either a moiety specific for it or to an antibody raised against it. In protein-ligand binding, the ligand is usually a signal-triggering molecule, binding to a site on a target protein. In DNA-ligand binding, a ligand is usually any small molecule or ion or even a protein that binds to the DNA double helix. The binding occurs by intermolecular forces, such as ionic bonds, hydrogen bonds and van der Waals forces. The docking (association) is usually reversible (dissociation). Incorporation of such ligands into a block copolymer, which is in the form of a hierarchically porous film, allows for the capture and purification of a particular biomolecular moiety by affinity chromatography using the appropriate affinity ligand. In one embodiment, Protein A is an affinity ligand attached to the block copolymer via chemical reaction either directly or through a linking molecule. The resulting films that have covalently bound Protein A can be used to capture or purify human immunoglobulin (IgG). Other embodiments of affinity ligands are Protein G, Protein A/G and Protein L. Still other examples of affinity ligand/target moiety include biotin (ligand)-streptavidin (moiety), digoxigenin (ligand)-anti-DIG-antibody and dinitrophenol (ligand)-anti-DNP-antibody, and nucleic acids. For covalent attachment of affinity ligands, examples of suitable functional groups on the material surface are: carboxylic acids, hydroxyl groups, amino groups, thiol groups and other groups that contain an ionizable or removable hydrogen. An embodiment of the covalent attachment of an affinity ligand is the attachment of Protein A to a carboxylic surface of a film. This is achieved by first activating the MBP material surface with 1-ethyl-3-(3-dimethylaminopropyl) carbodiimide chloride (EDC). Subsequently the activated material surface is exposed to the affinity ligand (Protein A), forming a covalent attachment of the ligand to the material surface.

Suitable linking agents include, but are not limited to, an imidoester such as dimethyl suberimidate; a N-hydroxysuccinimide-ester such as BS3; carbodiimides such as EDC, SMCC or its water-soluble analog, sulfo-SMCC, DCC or DIC; benzotrizole derivatives such as BOP, HATU, PyBOP and the like; anhydride or mixed anhydride formation via acid halides, acyl azides or sulfonyl halides; or an intermediate nitrophenyl ester. Although carboxylic acids are preferred, other coupling agents may be used when other kinds of functional groups exist on the block copolymer or block copolymer film.

In another embodiment, the MBP material bears a moiety selected from the group consisting of: a chemically reactive group suitable for reaction with a reactive group of a graftable compound to covalently graft the compound to the material; a pH sensitive group, a group suitable for direct immobilization of an analyte; a dye, fluorophore, chromophore, or quencher; an immobilized protein; and immobilized natural or artificial nucleic acid molecules.

In another embodiment, the MBP material comprises at least one of the following side chains or groups: hydroxyl, amino, carboxyl, polyethylene glycol, alkyl, maleimide, succinimide, acyl halide, sulfhydryl, or azide.

In another embodiment at least one functionalized monomer is an amino methacrylate, an amino acrylate, acrylic acid, dimethyl acrylamide, or methacrylic acid.

In another embodiment, the MBP material surface is modified with affinity ligand by non-covalent attachment, e.g. adsorption or impregnation.

In another embodiment of the invention the MBP material is the separation media for affinity-based separations, e.g. protein purification, which is used as a bind-and-elute operation where the target species is bound to the affinity ligand to isolate it. Subsequently, the target species can be unbound from the material to record the target species. In another embodiment of this invention binding a specific impurity is used to remove this impurity from a mixture while the target compound(s) flow through the material.

Another application of the invention is as part of a sensor, e.g. chemical or biochemical detection and/or quantification. Activation of a particular response on the film, resistance, capacitance, color, upon binding of a target species to the affinity ligand. In this embodiment, the binding of the target species to the affinity ligand invokes a detectable change or response of the material (e.g. change in spectrophotometric profile of membrane), allowing the detection and/or quantification of the target species.

One or more blocks of the MBP films of the invention are modified with a linker that provides functionality for the subsequent attachment of an affinity ligand; the MBPs of the invention have a three-dimensional block copolymer structure encompassing hierarchical porosity and modified with a linker or affinity ligand, and is not limited to the aspect ratio typical of a "film" or "membrane." The MBP material may be a monolithic material. The material may be molded or otherwise formed into various three-dimensional shapes. The shapes may contain zones with different porosities or ligands. The modification of the block copolymer with affinity ligand or linker is provided before or after fabrication into a film. The block copolymer modified with linker or affinity ligand relative to the stoichiometry of the block copolymer, by varying the time, temperature, concentration of modifier, etc. The relevant range or degree of modification for most applications is 10-100% of available sites. The MBP films of the invention include more than one affinity ligand or linker, an affinity ligand or linker containing more than one functionality, or affinity ligand or linker in part or completely on more than one polymer block.

The MBP ligand bearing materials/films of the present invention include conformal coatings of linking material by covalent or non-covalent means, resulting in a physical layer of the linker or affinity ligand; formation of or immobilization of the material on a support material, to provide mechanical stability.

The MBP ligand bearing materials/films of the present invention include integration into textiles, or a sensor device.

The MBP ligand bearing materials/films of the present invention further include micropores in the mated al/structure, in addition to its mesopore structure, provided by the processing of the MBP to incorporate microporous material into/onto the material/structure (e.g. zeolite, microporous carbon). The micropores are in addition to the mesopores, or replace, in-part or total the micropores provided by the mesopores.

The MBP films of the invention facilitate control of the geometry and area of material/structure that is modified with affinity ligand or linker. The geometric control is two-dimensional or three-dimensional, or some combination thereof. One embodiment of this geometric control of coating may be patterning, e.g. lithographically. Another embodiment of this geometric control is physically attaching a portion or portions of modified material/structure to unmodified film, or another substrate.

REFERENCE SUBJECT MATTER
INCORPORATED IN THEIR ENTIRETY

Low D, O'Leary R, Pujar N S. Future of antibody purification. *J Chromatogr B Analyt Technol Biomed Life Sci.* 2007; 848 (1):48-63.

Warner T, Nochumson S, Tripathi B P, Kumar M, Shahi V K. A Work in Process: Membrane-Based Chromatography. *Modern Drug Discovery.* 200345-49.

Chen C. Challenges and opportunities of monoclonal antibody manufacturing in China. *Trends in Bio/Pharmaceutical Industry.* 2009; 5 (3)

Palma A D. Downstream Process Bottlenecks onlineliebertpubcom. 2013

Janson J-C. Protein purification principles, high resolution methods, and applications. 3rd ed. Hoboken, N.J.: John Wiley & Sons;

Shukla A A, Hubbard B, Tressel T, Guhan S, Low D. Downstream processing of monoclonal antibodies—application of platform approaches. *Journal of Chromatography B.* 2007; 848 (1):28-39.

Shukla A A, Thommes J. Recent advances in large-scale production of monoclonal antibodies and related proteins. *Trends Biotechnol.* 2010; 28 (5):253-261.

Liu H, Fried J R. Breakthrough of lysozyme through an affinity membrane of cellulose-cibacron blue. *AIChE journal.* 1994; 40 (1):40-49.

Ghosh R. Protein separation using membrane chromatography: opportunities and challenges. *Journal of Chromatography A.* 2002; 952 (1): 13-27.

Amatani T, Nakanishi K, Hirao K, Kodaira T. Monolithic periodic mesoporous silica with well-defined macropores. *Chemistry of materials.* 2005; 17 (8):21 14-21 19.

Nakanishi K, Tanaka N. Sol-gel with phase separation. Hierarchically porous materials optimized for high-performance liquid chromatography separations. *Accounts of chemical research.* 2007; 40 (9): 863-873.

Nakanishi K, Amatani T, Yano S, Kodaira T. Multiscale Templating of Siloxane Gels via Polymerization-Induced Phase Separation†. *Chemistry of Materials.* 2007; 20 (3): 1108-1 115.

Sai H, Tan K W, Hur K et al. Hierarchical porous polymer scaffolds from block copolymers. *Science.* 2013; 341 (6145):530-534.

U.S. Pat. No. 9,464,969 B2 Titled "Monoliths" by Oberg et al.

What is claimed as new and desired to be protected by Letters Patent of the United States is:

1. A self-assembled polymer material comprising:
    at least one of mesopores or micropores; and
        wherein at least some of the mesopores are isoporous; and/or
        wherein at least some of the micropores are isoporous;
    a macroporous continuous domain comprising mesoporous walls;
    at least one multi-block polymer comprising at least two of the chemically distinct polymer blocks;
        wherein at least one polymer block of the multi-block polymer is a hydrophobic block;
        wherein at least one polymer block of the multi-block polymer is a hydrophilic block;
        wherein at least one polymer block of the multi-block polymer is covalently modified with a linking moiety,
        wherein an affinity ligand is covalently bound to the linking moiety; and
        wherein the affinity ligand is a protein; and
        wherein the affinity ligand can bind a target species.

2. The self-assembled polymer material of claim 1, wherein the material is asymmetric.

3. The self-assembled polymer material of claim 1, wherein the multi-block polymer is a three-dimensional block terpolymer structure encompassing hierarchical porosity.

4. The self-assembled polymer material of claim 1, wherein one of the at least two chemically distinct polymer blocks comprises poly((4-vinyl)pyridine).

5. The self-assembled polymer material of claim 1, wherein the linking moiety is formed by activating the multi-block polymer surface with a carbodiimide.

6. The self-assembled polymer material of claim 1, wherein more than one of the polymer blocks comprise the affinity ligand and linking moiety.

7. The self-assembled polymer material of claim 1, wherein the affinity ligand comprises more than one affinity ligand.

8. An article containing the self-assembled polymer material of claim 1, comprising the material immobilized on a support material to provide mechanical stability.

9. An article containing the self-assembled polymer material of claim 1, comprising the material integrated with a textile.

10. A sensor comprising the self-assembled polymer material of claim 1.

11. A device comprising the self-assembled polymer material of claim 1 in which the self-assembled polymer material is formed into a pleated pack, as flat sheets in a crossflow cassette or module, or in a spiral wound module.

12. A process of separating and/or detecting an analyte of interest, the method comprising:
contacting a medium comprising the analyte of interest with the self-assembled polymer material of claim 1.

13. The process of claim 12, wherein the analyte of interest is a protein.

14. The process of claim 12 wherein the separating comprises bind-and-elute operations where the analyte is a target species and is bound to the affinity ligand to isolate it, wherein the target species can be unbound from the material to record the target species.

15. The process of claim 12, wherein the analyte comprises a nucleic acid.

16. A method of detecting an analyte, the method comprising:
contacting a sensor with the analyte; and
measuring an optical/electrical change as a result of an interaction between the analyte or species of interest and the affinity ligand;
wherein the sensor comprises the self-assembled polymer material of claim 1; and
wherein the contacting the sensor is contacting the self-assembled polymer material.

17. A process utilizing a device according to claim 11 for the separation of molecules or suspended particles, the process comprising:
binding the molecules or suspended particles to the self-assembled polymer material;
eluting the molecules or suspended particles from the self-assembled polymer material; and
wherein the binding and the eluting are carried out by filtration.

* * * * *